United States Patent [19]

Davis

[11] Patent Number: 4,592,728
[45] Date of Patent: Jun. 3, 1986

[54] PERIODONTAL LAVAGE DELIVERY SYSTEM

[76] Inventor: Dennis R. Davis, 700 Moraga St., San Francisco, Calif. 94122

[21] Appl. No.: 604,608

[22] Filed: Apr. 30, 1984

Related U.S. Application Data

[63] Continuation of Ser. No. 328,000, Dec. 7, 1981, abandoned.

[51] Int. Cl.$^4$ .............................................. A61M 5/00
[52] U.S. Cl. .......................................... 433/80; 433/81
[58] Field of Search .................... 209/81; 433/80, 81; 128/218, 240, 62 A, 272, 276, 347

[56] References Cited

U.S. PATENT DOCUMENTS

| | | | |
|---|---|---|---|
| 3,346,958 | 10/1967 | Sinatra et al. | 433/80 |
| 3,921,297 | 11/1975 | Vit | 433/80 |
| 4,247,288 | 1/1981 | Yoshii | 433/224 |
| 4,249,899 | 10/1981 | Davis | 433/32 |
| 4,276,880 | 7/1981 | Malmin | 433/80 |
| 4,364,730 | 12/1982 | Axelsson | 433/141 |

FOREIGN PATENT DOCUMENTS 3033483 6/1982 Fed. Rep. of Germany ........ 433/80

Primary Examiner—Robert Peshock
Attorney, Agent, or Firm—Townsend & Townsend

[57] ABSTRACT

Collected bacteria in a deep periodontal pocket may be treated without the need for periodontal surgery by introducing a delivery instrument into the pocket through its open end, and then delivering a bactericidal solution to the bottom of the pocket through the delivery instrument. The delivery instrument comprises a capillary tube formed with an elbow at a predetermined distance from its distal end and adapted at its proximal end for detachable connection to a grip member and duct means communicating with a source of therapeutic fluid, the flow of which is controlled by the user.

1 Claim, 4 Drawing Figures

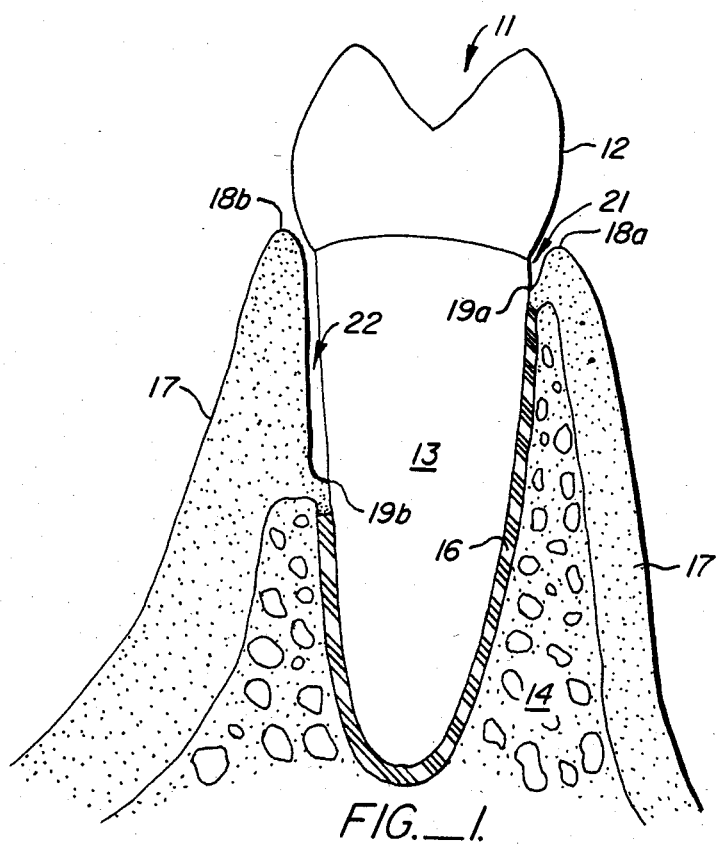
FIG._1.
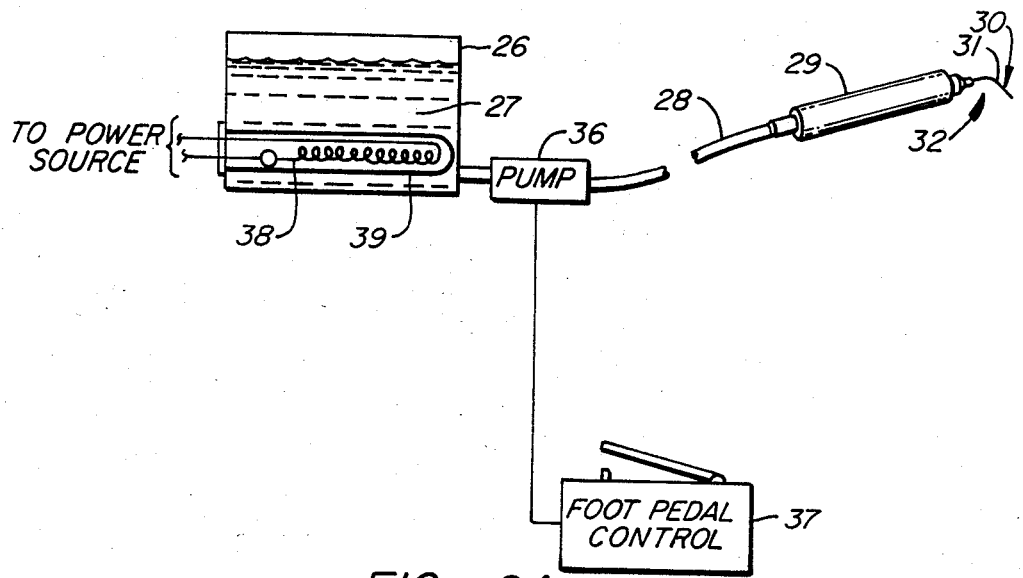
FIG._2A.

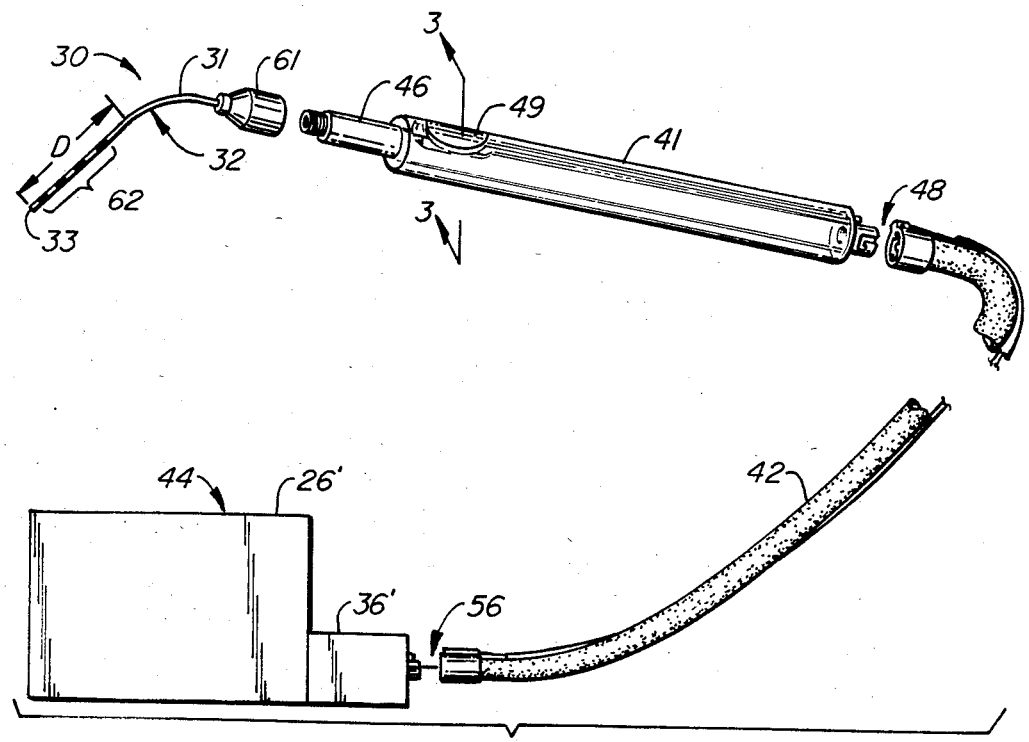
FIG._2B.
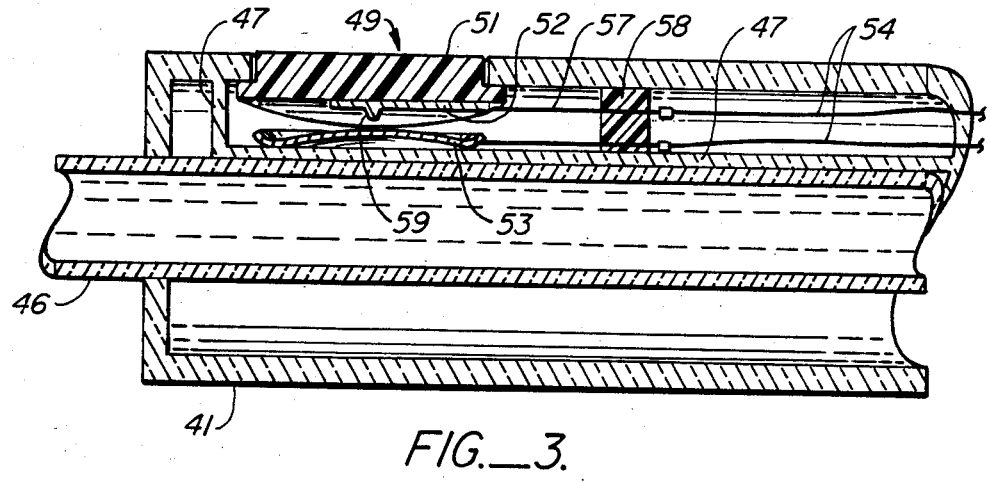
FIG._3.

PERIODONTAL LAVAGE DELIVERY SYSTEM

This is a continuation of application Ser. No. 328,000, filed Dec. 7, 1981, now abandoned.

BACKGROUND OF THE INVENTION

The invention relates generally to dental hygiene and in particular to a method and apparatus for cleaning periodontal pockets.

Until recently, it had generally been felt that proper cleaning of the teeth and regular visits to a dental hygienist would adequately guard against tooth decay and gum disease. Tooth decay is caused by bacteria which are adhered, or in essence glued, to the teeth in a matrix known as bacterial plaque. Regular cleaning guards against decay by preventing the buildup of plaque. However, certain gum diseases, for example, forms of chronic generalized periodontitis or juvenile periodontosis, have been observed to arise without substantial accompanying plaque, thus indicating that typical bacterial plaque is not the primary causative agent.

Unlike tooth decay, in which the decay-causing bacteria are adhered to the teeth by the plaque, it now appears that some types of periodontal diseases are associated with bacteria which accumulate in periodontal pockets. These pockets develop under the action of bacteria or other irritants and toxins collected in the shallow regions normally found between the teeth and gums. Bacteria proliferating within a pocket gradually lead to the destruction of the structures supporting the teeth and cause the pocket to deepen. With extensive degeneration of the bone and periodontal ligament adjacent the root of a tooth, a pocket can develop to depths of 12 millimeters or more.

Conventional modes of dental hygiene—tooth brushes, tooth picks and the like—are ineffective for cleaning out periodontal pockets; they merely scrape food and plaque from around the teeth. A dentist working with specially designed instruments can reach and partially clean out shallower pockets. In the acute situation in which an abscess develops in a deeper pocket, surgical methods are called for to clean out the infection. Moreover, even the use of antibiotics to treat periodontal infection is limited because of the ineffectiveness of systemic or topical methods of application within the mouth. In short, no method of lavation or other non-surgical treatment is known which can penetrate and fully cleanse the deeper periodontal pockets.

SUMMARY OF THE INVENTION

The present invention provides a method and apparatus for cleansing even the deepest of periodontal pockets. The method can be practiced by an individual in the home as a preventive measure against gum disease, and it can be practiced by a dentist to treat developing disease. The invention enables one to deliver a bactericidal solution, antibiotic, or other therapeutic substance to the depths of a periodontal pocket with no resulting trauma to the surrounding tissue.

Briefly, the method of the present invention comprises the steps of introducing a thin tube through the entrance to a pocket and alongside the root of the tooth, and then delivering a bactericidal solution into the pocket through the tube. With a sufficiently narrow gauge tube, the bactericidal solution can be delivered directly to the lower regions of a pocket, no matter how deep, where pathogenic bacteria tend to proliferate.

The apparatus of the invention may be embodied in a form for home use or in a form more convenient for use by a dental hygienist or dentist. Briefly, the apparatus comprises a grip member, a delivery tip fixed to the grip member, and duct means communicating with the delivery tip. The delivery tip is formed of a narrow gauge capillary tube with an elbow at a predetermined distance from its distal end to facilite insertion into a periodontal pocket. The duct means are adapted for connection to a source of therapeutic lavage fluid, such as a bactericidal solution.

The invention is used in conjunction with a base unit containing reservoir means for holding the therapeutic fluid and means for actuating flow of the fluid from the reservoir means to the delivery tip fixed to the grip member. In the embodiment of the invention for home use, manually engageable switch means are mounted on the grip member and adapted for connection to the means in the base unit for actuating the fluid flow. In the embodiment intended for use by a trained professional, the means for actuating fluid flow may more conveniently be controlled by a foot pedal, rather than switch means mounted on the grip member.

It is an object of the invention to provide a delivery tip which can readily be detached for cleaning and sterilization, and which can be exchanged for longer or shorter tips as called for.

A further understanding and appreciation of the scope and advantages of the invention can be gained from the following specification and attached drawings.

BRIEF DESCRIPTION OF THE DRAWINGS

FIG. 1 is an illustration of a tooth and supporting structures showing both healthy and diseased periodontium.

FIG. 2A is a diagrammatic illustration of apparatus constructed in accordance with the invention.

FIG. 2B is an illustration of an alternative embodiment of the present invention.

FIG. 3 is an enlarged cross-sectional view of a portion of the grip member of FIG. 2B, showing switch means.

DETAILED DESCRIPTION OF THE PREFERRED EMBODIMENTS

The method and apparatus of the invention can best be appreciated after a description of the supporting structures of the teeth. FIG. 1 shows a tooth 11 together with its supporting structures, known as the periodontium. Tooth 11 has a crown 12 and root 13 implanted within a socket in bone 14. The root 13 is secured to bone 14 by means of the periodontal ligament 16. Surrounding the outer surfaces of bone 14 is the gingival tissue 17 forming the gums. In a healthy periodontium, the gingival tissue follows the contour of bone 14 to form a crest at 18a and attaches to root 13 at a point 19a at or slightly below the base of crown 12. Even in a healthy periodontium a slight pocket 21 is formed from crest 18a to attachement point 19a. Even a very shallow pocket 21 will tend to collect harmful bacteria, which unless eliminated will eventually cause damage to the periodontium.

In the diseased periodontium illustrated on the left side of FIG. 1, extensive degradation of bone 14 and periodontal ligament 16 has occurred. The gingival crest 18b remains approximately at its former height but the gingival tissue attaches at a point 19b much farther along the root 13 to form a deep periodontal pocket 22.

The pocket 21 occurring in a healthy periodontium is typically one to two millimeters in depth. Pockets occuring in diseased periodontia have been known to grow as deep as 13 millimeters or more.

Bacteria lodged within periondontal pockets are not flushed out in the normal course of brushing the teeth or in other conventional methods of dental hygiene. In fact, anaerobic bacterial species, such as Bacteroides, Fusobacterium or Actinomyces, have been observed in deeper pockets, indicating that the lower reaches of deep pockets are impervious even to the plentiful supply of oxygen found in the mouth. Occasionally, the gingival tissue forming the wall of a deep pocket will become deformed, so that the gingival crest 18a contacts the root of the tooth to close off the entrance to the pocket, making the pocket even more inaccessible to conventional modes of treatment.

The present invention provides apparatus for delivering a bactericidal or other solution to the bottom of even the deepest and most inaccessible of periodontal pockets.

FIG. 2A shows an embodiment of the invention preferred for use in a dentist's office. Reservoir means 26 holds a supply of therapeutic solution 27 of cleansing, flushing, or otherwise treating the periodontal pockets. In flow communication with the reservoir means 26 is duct means 28, which may be provided for example by Tygon tubing. Secured to an end of the duct means 28 is a grip member 29. Secured, in turn, to an end of grip member 29 is a delivery tip 30 comprising a length of narrow-gauge capillary tube 31. Twenty-five to thirty gauge dental syringe tubing is suitable for this purpose. As best seen in the enlarged view of FIG. 2B, capillary tube 31 is provided with an elbow 32 at a predetermined distance D from its distal end 33. The tube 31 is preferably formed of stainless steel to guard against corrosion. The apparatus is provided with means, such as pump 36, for actuating the flow of fluid 27 from reservoir means 26 to delivery tip 30. As will be appreciated by those skilled in the dental arts, when assiduously attending to a patient, it is expedient to operate pump 36 by means of a foot pedal control 37.

As explained in more detail hereinbelow, grip member 29 can be manipulated to insert capillary tube 31 into a periodontal pocket for delivery of the therapeutic fluid 27. To prevent shock to the surrounding tissue or nerves of the teeth, it is advantageous to provide reservoir means 26 with means for regulating the temperature of the fluid contained therein. In the embodiment of FIG. 2A reservoir means 26 is provided with an electrically powered heating element 38 enclosed within casing 39 and positioned in the interior of reservoir means 26.

An embodiment of the invention more suitable for home use is shown in FIG. 2B. Delivery tip 30 is detachably mounted to grip member 41, which may also be detachably connect to duct means 42. The duct means 42 is in turn detachably connected to a base unit 44, which includes reservoir means 26' and electric pump 36'.

Grip member 41 is constructed with duct means comprising an inner conduit 46 running from one end to the other to connect duct means 42 with delivery tip 30. As a safety measure, grip member 41 includes an interior chamber defined by wall 47 to isolate the electrical connections for controlling pump 36' from potential fluid leaks at connector 48 at the posterior end of grip member 41.

In the embodiment for home use, manually engageable switch means 49 are mounted on grip member 41 and adapted at connector 48 for electrical connection to pump 36'. In the preferred form of this embodiment, switch means 49 comprise a touch-sensitive switch positioned on grip member 41 to be actuated by finger or thumb pressure when grip member 41 is grasped for use. FIG. 3 shows a touch-sensitive switch including flexible plastic member 51 mounted within an aperature in grip member 41. Fixed to the underside of flexible member 51 is metal contact 52. Metal contact 53 is mounted on wall 47 opposite contact 52. The contacts 52 and 53 are connected to electric pump 36' by wires 54 through standard detachable connectors 48 and 56. Contact 52 is supported by spring bar 57 fixed at one end within plastic mounting 58. In operation, flexible member 51 is depressed by slight finger pressure, bringing boss 59 on contact 52 into electrical engagement with contact 53 to close the circuit.

The same delivery tip 30 may be used in the home or the dentist's office. As indicated above, the tip 30 comprises a capillary tube 31, which is preferably adapted at its proximal end for detachable connection to grip member 29 or 41. In the embodiment of FIG. 2B, capillary tube 31 is provided with screw connector 61 for this purpose, although other types of adaptation may be made. As described herein, the periodontal delivery tip 30 of the present invention is used with apparatus supplying a pressurized fluid. With appropriate adaptation the delivery tip of the present invention can be used with known apparatus supplying a pressurized fluid for water picks and the like; the present delivery tip thus enables one to convert existing apparatus to use in cleansing periodically pockets as described hereinbelow.

To practice the method of the present invention, delivery tip 30 is introduced into a periodontal pocket without puncturing the gingival tissue 17 by guiding the distal end 33 along the root 13 of the tooth. Even though gingival crest 18b may bridge the entrance to the pocket, the unsharpened distal end of the tip may generally be maneuvered past the crest without puncturing it. Once the tip has been introduced into the periodontal pocket, the therapeutic fluid can be dispensed. This will be accomplished by means of the foot pedal control 37 in the embodiment of FIG. 2A or by means of the manually engageable switch 49 in the embodiment for home use in FIG. 2B.

Delivery of the fluid to the pocket serves to flush out accumulated bacteria. However, a mere flushing action, although beneficial, is insufficient to cleanse the pocket completely and prevent the spread of disease. For effective treatment it is necessary to flush the pocket with a bactericidal solution. Suitable for this purpose are, for example, a solution of at least 6.5% by weight of sodium chloride or a saturated or near-saturated solution of sodium bacarbonate. More than mere flushing action, the bactericidal solution provides a lingering therapeutic benefit.

It has been found advantageous to warm the bactericidal solution before introducing it into a pocket. A temperature of about 43° C. has been found suitable. This provides for patient comfort and prevents shock to the nerves of the teeth. Moreover, the warmer temperature helps to hold the sodium chloride in solution and generally makes the solution more active chemically.

To assure effective treatment of especially deep and inaccesible pockets, it is important that the delivery tip be inserted to the bottom region of the pocket. For this purpose, delivery tip 30 is provided with indicia of the distance from its distal end 33. For example, as shown in FIG. 2B capillary tube 31 is color-coded by means of alternating bands 62, each band indicating typically two millimeters of depth. The coded tip is then used in conjunction with a similarily coded probe. First, the probe is inserted into the pocket to plumb the depth. Then the tip may be inserted to the bottom of the pocket, as indicated by the markings 62.

It is seen that the present invention provides a method and instrumentation for delivering therapeutic solutions to the depths of a periodontal pocket without the need of surgery and without piercing the surrounding tissue. As disclosed hereinabove, the method and instrumentation are used to deliver a saline solution or other bactericidal solution to the pocket. Other substances, as called for by different treatment protocols, may of course also be delivered in accordance with the present invention. For example, the invention may be used for the localized placement of antibiotics within a periodontal pocket.

In summary, it is seen that the present invention enables an individual for the first time to take preventive measures against the onset of gum disease by regular hygiene practiced in the home. It also enables a periodontist to treat various abnormal conditions, such as a typical periodontitis, simply and quickly without the need for periodontal surgery.

While the above provides a full and complete description of the preferred embodiments of the present invention, various modifications, alternate constructions, and equivalents will occur to one skilled in the art given the benefit of this disclosure. Such modifications and alternate constructions are considered to fall within the spirit and scope of the invention disclosed herein, which is defined by the appended claims.

What is claimed is:

1. Apparatus for use in therapeutic lavage of periodontal pockets comprising:
    a generally cylindrical grip member;
    a delivery tip comprising a base portion and a capillary tube fixed at the proximal end thereof to said base portion, said base portion being detachably mounted to said grip member, said capillary tube being formed of stainless steel of 25 to 30 gauge having a central bore opening directly into the distal end of said delivery tip, and having an elbow defining an obtuse angle in the range of 120 to 150 degrees at a predetermined distance of at least 10 mm from said distal end to facilitate insertion of said tube into a periodontal pocket, said capillary tube being further provided with indicia, in the form of alternately colored bands around said capillary tube, of the distance from said distal end;
    a base unit containing reservoir means for holding a therapeutic lavage fluid;
    electric pump means for actuating flow from said reservoir means;
    duct means in flow communication with said delivery tip and said reservoir means; and
    touch-sensitive switch means positioned on said grip member to be actuated by finger or thumb pressure when the grip member is grasped for use, said switch means being connection to actuate said electric pump means thereby producing a controlled flow of therapeutic lavage fluid from said reservoir means through said delivery tip for delivery to the depths of a periodontal pocket.

* * * * *